(12) United States Patent
Shoroji et al.

(10) Patent No.: US 8,142,346 B2
(45) Date of Patent: Mar. 27, 2012

(54) ENDOSCOPE WITH ELECTROMAGNETIC WAVE SHIELD

(75) Inventors: Ayanori Shoroji, Hino (JP); Katsushi Watanabe, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1284 days.

(21) Appl. No.: 11/880,273

(22) Filed: Jul. 20, 2007

(65) Prior Publication Data

US 2008/0021268 A1 Jan. 24, 2008

(30) Foreign Application Priority Data

Jul. 21, 2006 (JP) ................................. 2006-199973
Mar. 29, 2007 (JP) ................................. 2007-088973

(51) Int. Cl.
*A61B 1/04* (2006.01)
(52) U.S. Cl. ........................ 600/110; 600/131; 600/134
(58) Field of Classification Search .................. 600/134, 600/131, 109, 110
See application file for complete search history.

(56) References Cited

U.S. PATENT DOCUMENTS

| | | | | | |
|---|---|---|---|---|---|
| 4,750,477 | A | * | 6/1988 | Wardle | 600/153 |
| 4,974,075 | A | * | 11/1990 | Nakajima | 348/75 |
| 5,569,158 | A | * | 10/1996 | Suzuki et al. | 600/110 |
| 5,810,714 | A | * | 9/1998 | Takamura et al. | 600/134 |
| 5,876,326 | A | * | 3/1999 | Takamura et al. | 600/110 |
| 6,007,480 | A | * | 12/1999 | Iida et al. | 600/109 |
| 6,315,712 | B1 | * | 11/2001 | Rovegno | 600/109 |
| 6,319,197 | B1 | * | 11/2001 | Tsuji et al. | 600/132 |
| 6,387,043 | B1 | * | 5/2002 | Yoon | 600/109 |
| 6,419,626 | B1 | * | 7/2002 | Yoon | 600/109 |
| 6,590,470 | B1 | * | 7/2003 | Burdick | 333/28 R |
| 6,652,451 | B2 | * | 11/2003 | Murata et al. | 600/118 |
| 2003/0078476 | A1 | * | 4/2003 | Hill | 600/160 |
| 2004/0092793 | A1 | * | 5/2004 | Akai | 600/134 |
| 2004/0204628 | A1 | * | 10/2004 | Rovegno | 600/131 |
| 2006/0122460 | A1 | * | 6/2006 | Kamali | 600/120 |
| 2006/0183971 | A1 | * | 8/2006 | Haviv | 600/101 |
| 2007/0129604 | A1 | * | 6/2007 | Hatcher et al. | 600/136 |
| 2007/0249904 | A1 | * | 10/2007 | Amano et al. | 600/131 |

FOREIGN PATENT DOCUMENTS

| | | |
|---|---|---|
| EP | 0 739 602 A1 | 10/1996 |
| EP | 1 719 445 A1 | 11/2006 |
| EP | 1 736 094 A1 | 12/2006 |
| JP | 2005-237513 | 9/2005 |
| JP | 2005-342399 | 12/2005 |
| WO | WO 97/15144 | 4/1997 |
| WO | WO 2005/077252 A1 | 8/2005 |
| WO | WO 2005/099560 A1 | 10/2005 |

* cited by examiner

*Primary Examiner* — John P Leubecker
(74) *Attorney, Agent, or Firm* — Scully, Scott, Murphy & Presser, P.C.

(57) ABSTRACT

An endoscope including an insertion portion, an operation portion, an image pickup device provided in the operation portion, an image display device connected to the operation portion and provided with a monitor portion, an image processing portion such as an image pickup device control circuit processing an image pickup signal of a portion to be inspected picked up by the image pickup device, a cylindrical rotating shaft formed by an electromagnetic wave shielding member such as metal, slidably engaged with the operation portion, for rotatably connecting the operation portion and the image display device to each other, and an image pickup cable inserted through the rotating shaft and electrically connecting the image pickup device control circuit and the image pickup device to each other.

6 Claims, 13 Drawing Sheets

ENDOSCOPE WITH ELECTROMAGNETIC WAVE SHIELD

CROSS REFERENCE TO RELATED APPLICATION

This application claims benefit of Japanese Applications No. 2006-199973 filed on Jul. 21, 2006, and No. 2007-88973 filed on Mar. 29, 2007, the contents of each of which are incorporated by their reference.

BACKGROUND OF THE INVENTION

1. Field of the Invention

The present invention relates to an endoscope in which a display device which displays an endoscopic image picked up by image pickup means is provided at an operation portion.

2. Description of Related Art

As a light source of an endoscope, a light source lamp incorporated in a light source device, which is a peripheral device to which an endoscope is connected, has been known. When illumination light is supplied from the light source device to the endoscope, the illumination light emitted from the light source lamp is transmitted by a light guide fiber extended through the endoscope via an operation portion from a universal cord of the endoscope to the distal end of the insertion portion and then, radiated to a portion to be inspected from the distal end of the insertion portion.

Also, with the purpose of simplifying an entire endoscope device comprised by an endoscope and peripheral devices, an endoscope is known recently in which the light source is comprised by a light emitting diode, which is provided inside the endoscope, and a display device displaying an endoscopic image is connected to an operation portion.

With the configuration that the light source comprised by a light emitting diode is provided inside the endoscope, the light source device connected to the endoscope is not needed any more, which can simplify the endoscope device and also since the light emitting diode can emit light with saved power as compared with a light source lamp and the like, power saving of the endoscope device can be promoted. Also, with the configuration that the display device is connected to the operation portion, a monitor connected to the endoscope is not needed any more, which can simplify the endoscope device.

Moreover, inside the operation portion of the endoscope, an image pickup device such as CCD receiving an image (light) guided by an image guide and a light collecting lens for forming an image on a light receiving portion of the image pickup device are provided, and in the display device, an image processing circuit is provided such as an image pickup device control circuit outputting an image of a photographic subject picked up by the image pickup device converted into a signal.

There are many proposals made as prior arts of this type of endoscope device such as Japanese Patent Laid-Open No. 2005-237513 and Japanese Patent Laid-Open No. 2005-342399.

Japanese Patent Laid-Open No. 2005-237513 discloses a prior art relating to an endoscope device in which a grasping portion is provided and an operation portion connected to a proximal end of an insertion portion and a support portion provided at the operation portion and rotatably supporting the display device are provided, and by configuring a display screen of the display device rotatable around the axis crossing the longitudinal direction of the grasping portion, when an operator grasps the operation portion capable of operation, the display screen can be faced in a direction easy to be seen even if the direction of the operation portion is changed.

Japanese Patent Laid-Open No. 2005-342399 discloses a prior art relating to an endoscope device in which an endoscope with a grasping portion and a display device are integrally provided and is configured with an image display device mounted so as to protrude from the side portion of the endoscope so that the image display device is located on gripping fingers other than the thumb when the grasping portion is grasped with the thumb up. Then, weight balance is improved, a burden on fingers in use is reduced and operation is easy for a long time.

SUMMARY OF THE INVENTION

A first endoscope according to the present invention comprises an insertion portion to be inserted into a subject, an operation portion continuously provided on the proximal end side of the insertion portion, an image pickup device provided in the insertion portion or the operation portion for picking up an image of a portion to be inspected of the subject, a display device provided at the operation portion and provided with a display portion on which a picked up image of the portion to be inspected picked up by the image pickup device is displayed, an image processing portion provided at the display device for processing an image pickup signal of the portion to be inspected picked up by the image pickup device, and an electromagnetic wave shielding portion provided at a connection portion between the operation portion and the display device and in which an image pickup cable is arranged for electrically connecting the image processing portion and the image pickup device to each other.

A second endoscope according to the present invention comprises an elongated insertion portion to be inserted into a subject, an operation portion continuously provided on the proximal end side of the insertion portion, an image pickup device provided in the insertion portion or the operation portion for picking up an image of a portion to be inspected of the subject, a display device connected to the operation portion and provided with a display portion on which an endoscopic image of the portion to be inspected picked up by the image pickup device is displayed, an image processing portion provided at the display device for processing an image pickup signal of the portion to be inspected picked up by the image pickup device, a cylindrical shaft member provided at the display device and formed of an electromagnetic wave shielding member slidably engaged with the operation portion for rotatably connecting the operation portion and the display device to each other, and an image pickup cable inserted inside the shaft member and electrically connecting the image processing portion and the image pickup device to each other.

The above and other objects, features and advantages of the invention will become more clearly understood from the following description referring to the accompanying drawings.

DETAILED DESCRIPTION OF THE PREFERRED EMBODIMENT

An embodiment of the present invention will be described below referring to the accompanying drawings. In the embodiment below, a medical endoscope is used as an example of an endoscope.

Figure 1:
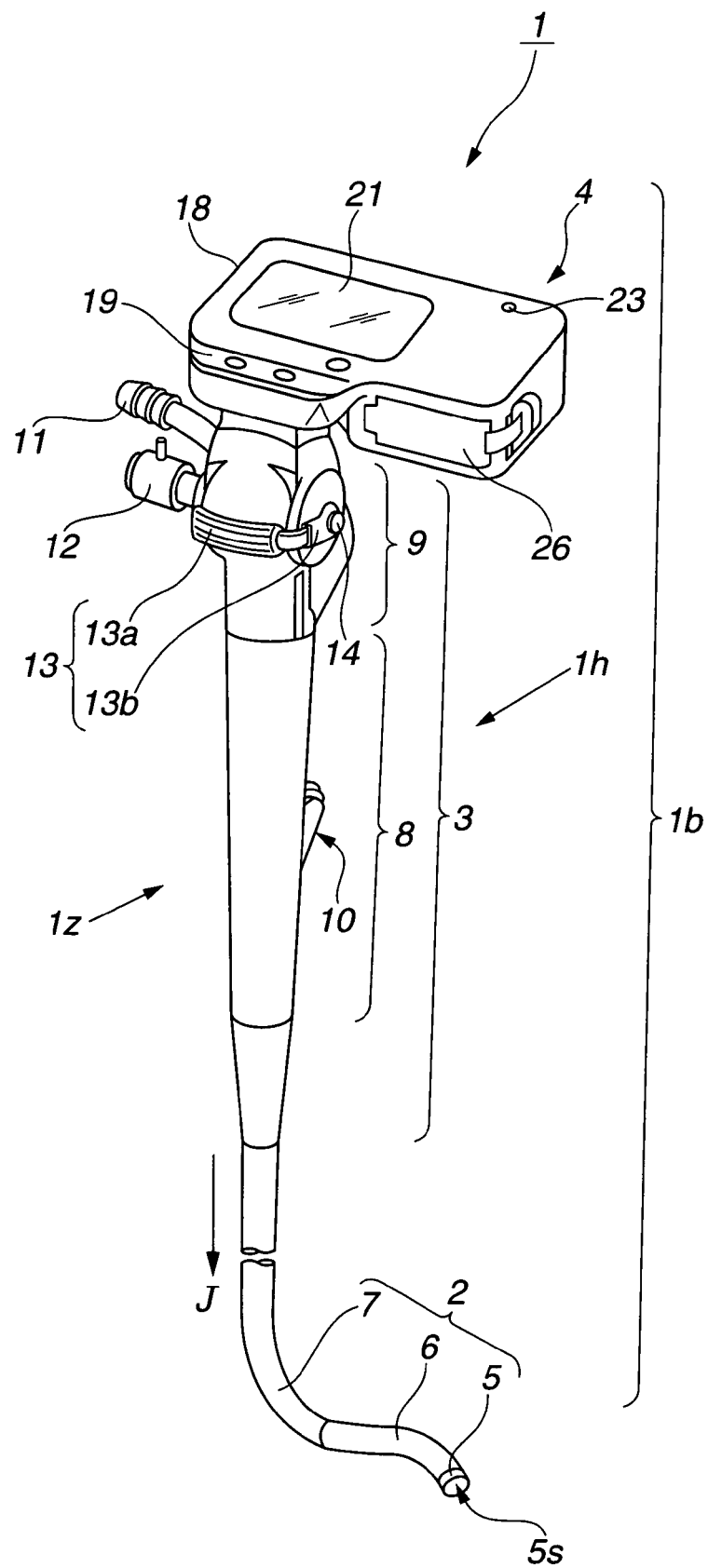
FIG. 1 is a perspective view of an endoscope illustrating an embodiment of the present invention.
Figure 2:
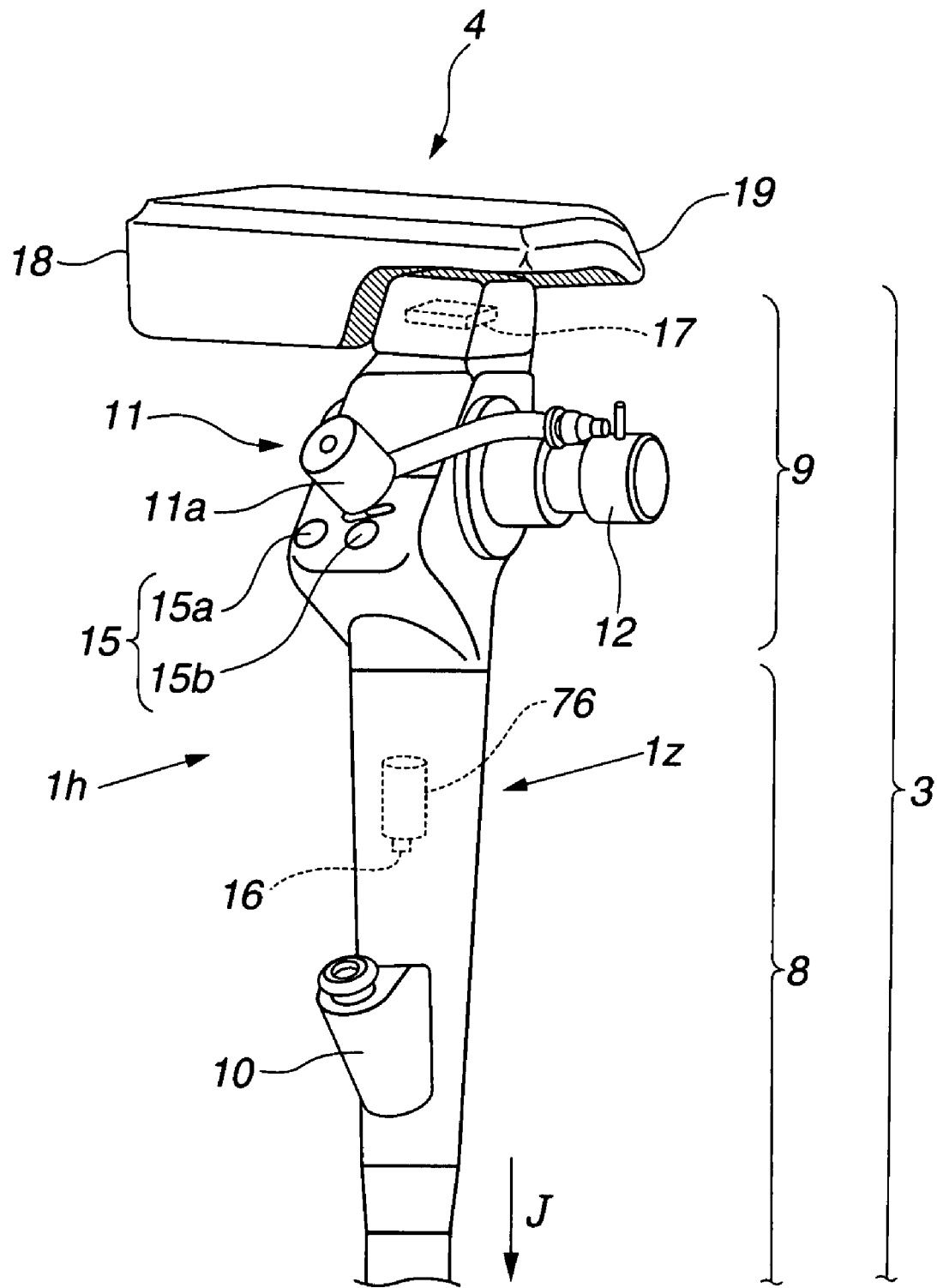
FIG. 2 is a partial perspective view of the endoscope in FIG. 1 seen from the front side.
Figure 3:
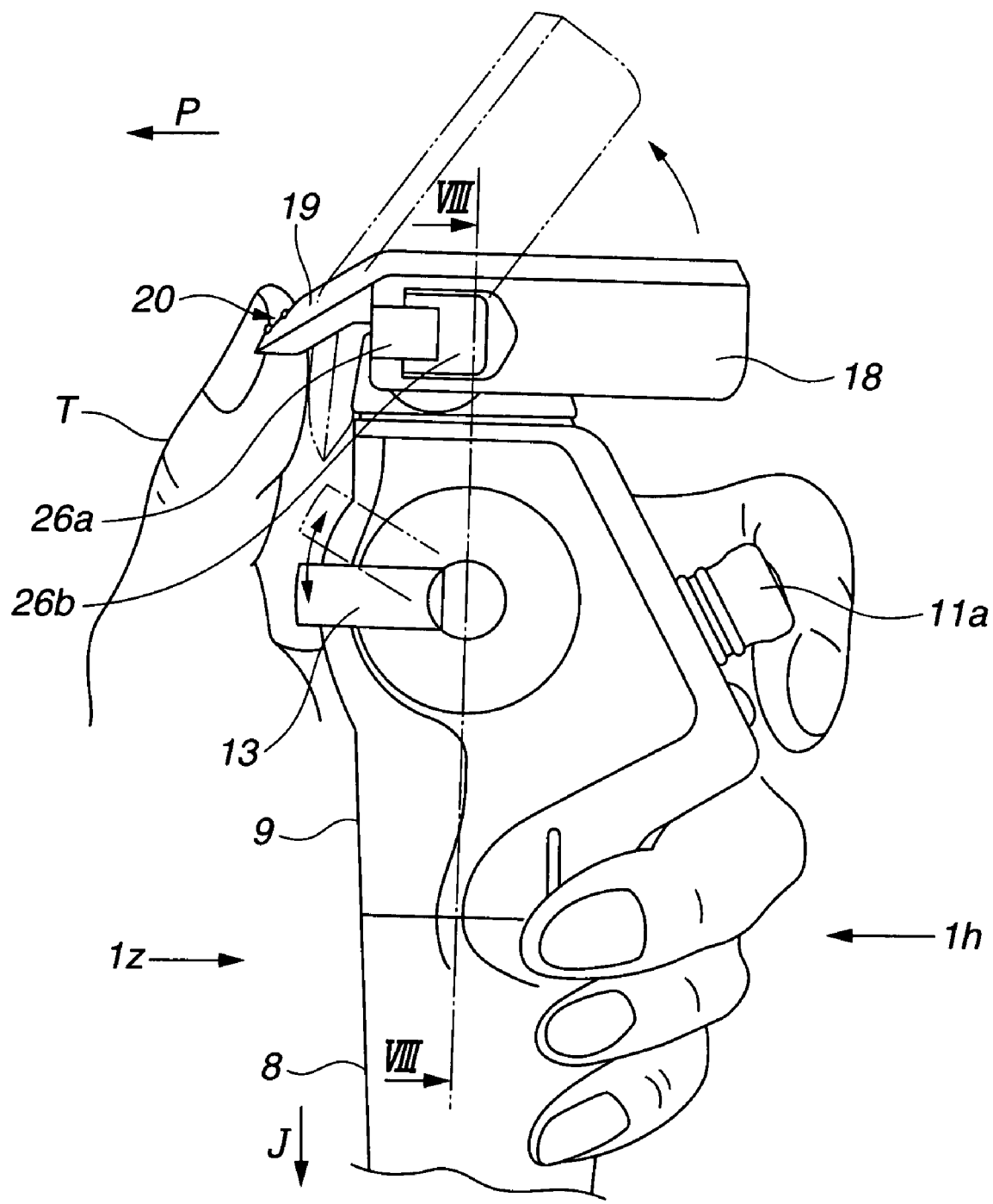
FIG. 3 is a partially enlarged plan view illustrating a state where an image display device of the endoscope in FIG. 1 is rotatable.
Figure 4:
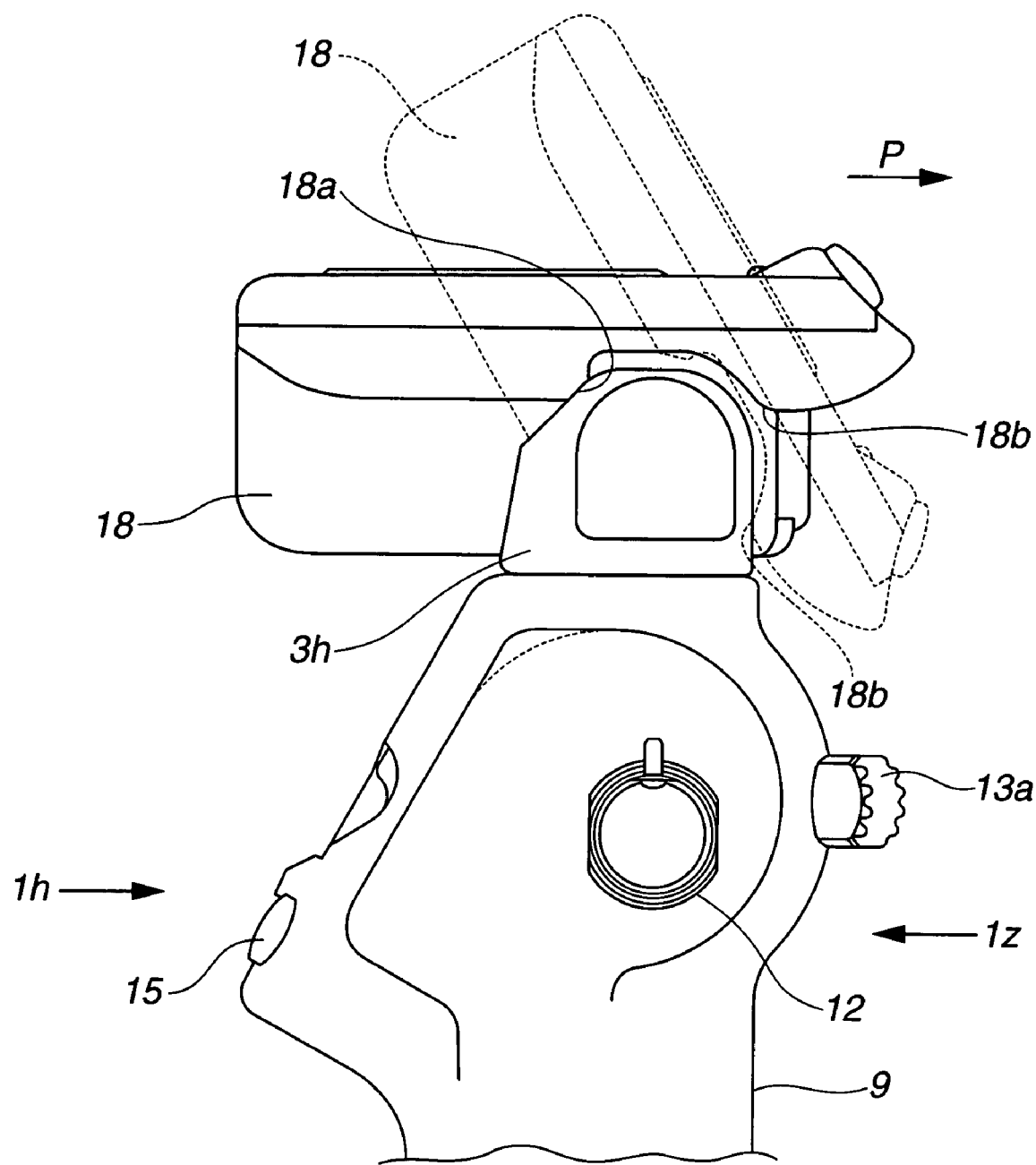
FIG. 4 is a partially enlarged plan view illustrating a state where rotation of the image display device of the endoscope in FIG. 1 is restricted.
Figure 5:
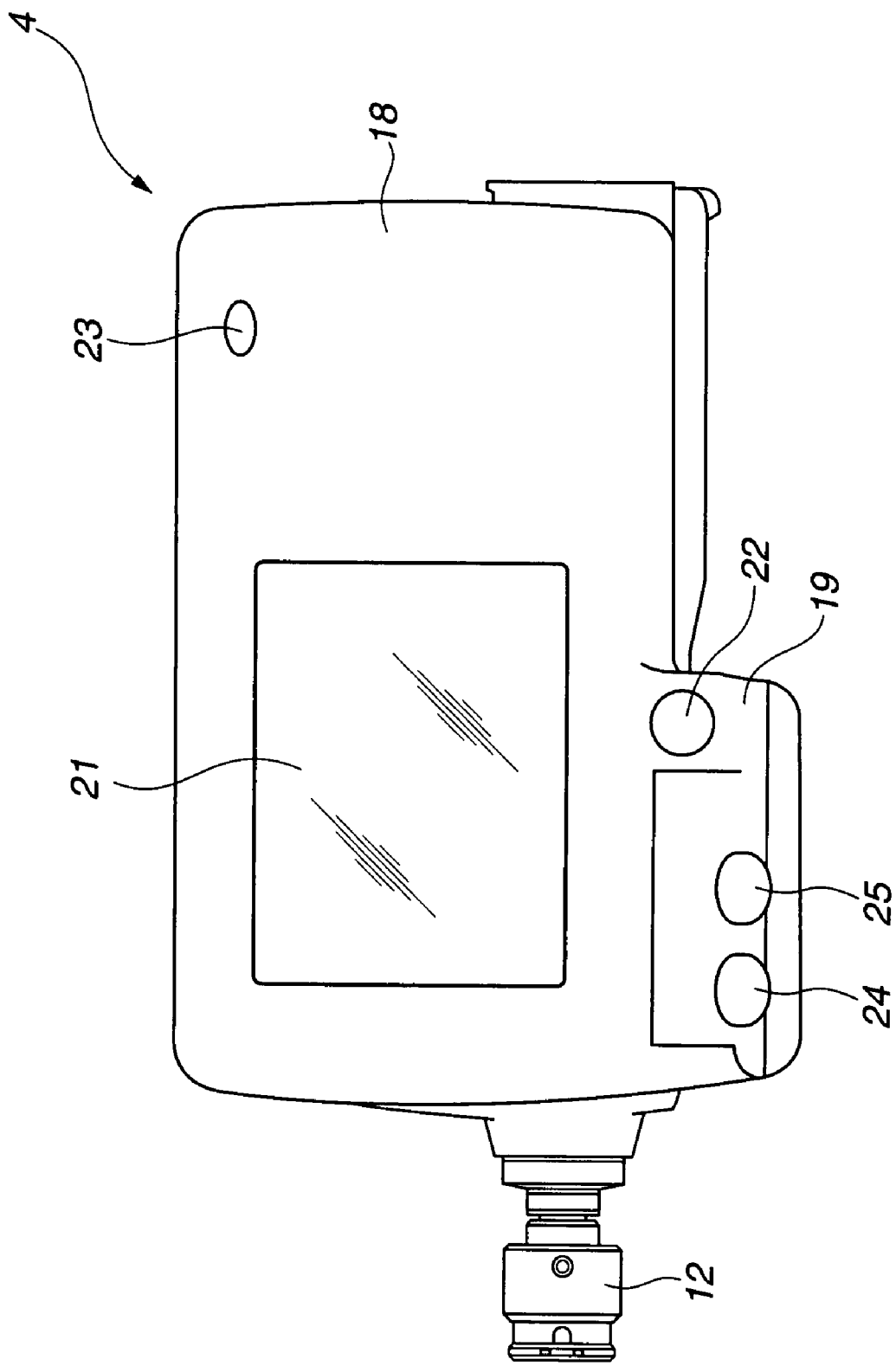
FIG. 5 is a plan view of the image display device of the endoscope in FIG. 1.

FIG. 1 is a perspective view of an endoscope illustrating an embodiment of the present invention, FIG. 2 is a partial perspective view of the endoscope in FIG. 1 seen from the front side in FIG. 1, FIG. 3 is a partially enlarged plan view illustrating a state where an image display device of the endoscope in FIG. 1 is rotatable, FIG. 4 is a partially enlarged view illustrating a state where rotation of the image display device in FIG. 3 is restricted, and FIG. 5 is a plan view of the image display device of the endoscope in FIG. 1.

As shown in FIG. 1, an endoscope body 1b of the endoscope 1 is mainly comprised by an insertion portion 2 inserted into a portion to be inspected within a body cavity to be a subject, an operation portion 3 continuously provided on the proximal end side of the insertion portion 2, and an image display device 4, which is a display device disposed at the upper end of the operation portion 3.

The insertion portion 2 is formed in an elongated shape having flexibility, and its major part is comprised by a rigid distal end portion 5 located on the distal end side, a bending portion 6 continuously provided on the proximal end side of the distal end portion 5, and a flexible portion 7 continuously provided on the proximal end side of the bending portion 6.

The operation portion 3 is mainly comprised by a grasping portion 8 grasped by an operator when the operator grasps the endoscope 1 and an operation portion main body 9 provided on the proximal end side of the grasping portion 8.

The grasping portion 8 is formed in the shape that can be held by the thumb T and the other fingers of the left hand of the operator, for example, (See FIG. 3) as if being wrapped around, in the rod state, for example. The grasping portion 8 may be formed in the shape that can be held by the right hand of an operator.

At the grasping portion 8, a treatment instrument insertion portion 10 is provided on a front 1h side of the endoscope 1, through which a treatment instrument is inserted into/removed from the body cavity by inserting/removing the treatment instrument such as forceps into/from a suction pipe line 100 (See FIGS. 6 and 7), which will be described later.

As shown in FIG. 2, on the front 1h side of the endoscope 1 of the operation portion main body 9, a suction base 11 used for suctioning a liquid such as a body fluid, sputum or the like from the body cavity is provided. To the suction base 11, a suction device can be freely connected via a tube, not shown.

Figure 7:
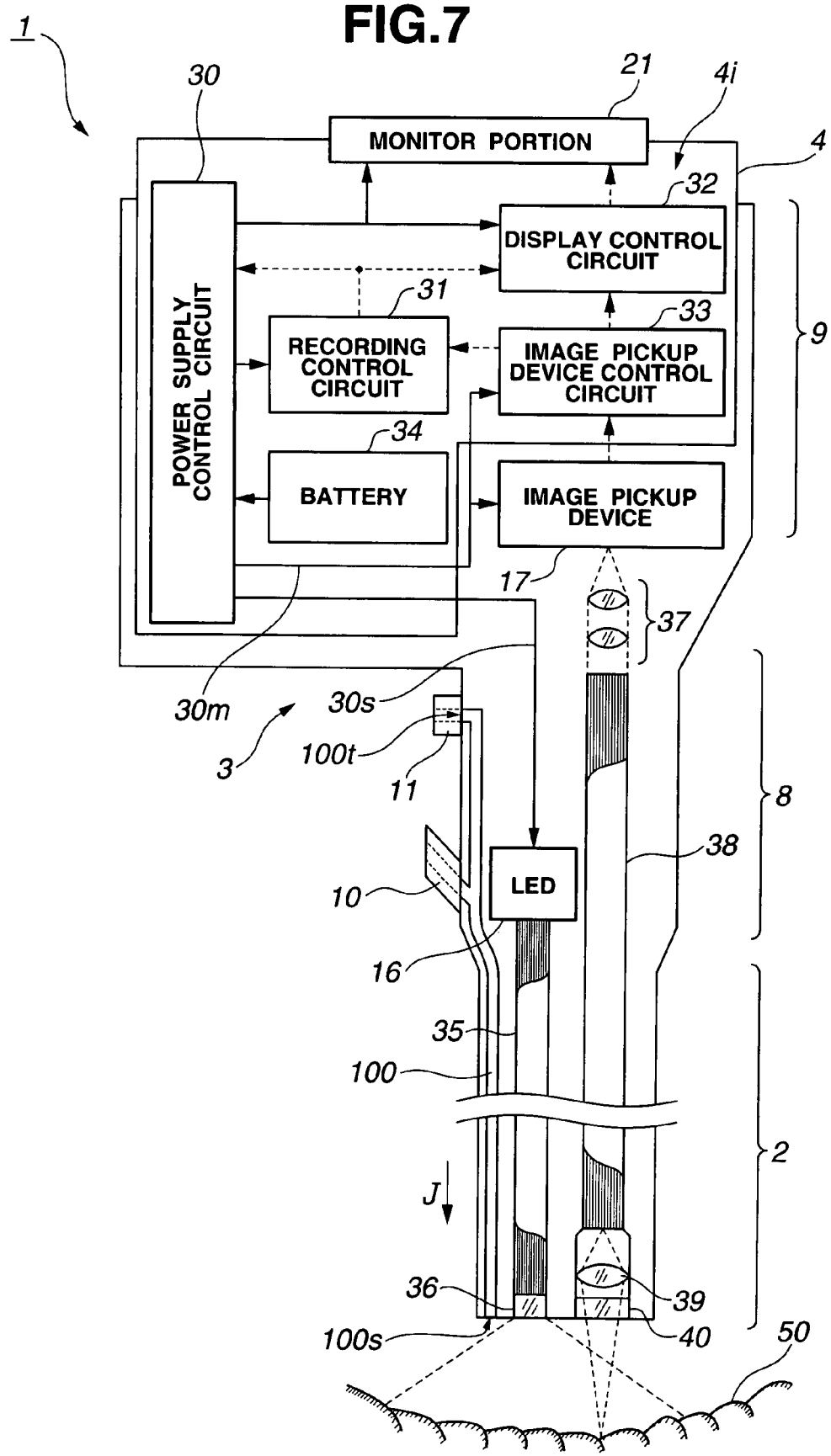
FIG. 7 is a block diagram schematically illustrating the internal configuration of the endoscope in FIG. 1 centered on an image pickup system and an illumination optical system.

The operator can suction the body fluid, sputum or the like from the body cavity by operating the suction device. More specifically, the operator can suction the body fluid, sputum or the like from the body cavity through the suction pipe line 100, which is a fluid pipe line, extended through the operation portion 3 and the insertion portion 2 so that one end 100t is opened at the operation portion main body 9 and the other end 100s is opened at a distal end face 5s of the distal end portion 5 as shown in FIG. 7, which will be described later, by operating a suction button 11a, which will be also described later. A tube may be inserted through a flow passage in the suction pipe line 100 so that an air supply device for supplying air into the body cavity can be connected to the tube at the suction base 11.

Also, on the left side in FIG. 1 of the operation portion main body 9, a ventilation base 12 is provided to be used at leakage inspection of the endoscope 1 for supplying air into the insertion portion 2, the operation portion 3, and the image display device 4. To the ventilation base 12, an air feeding device can be connected via a tube, not shown. An operator can conduct leakage inspection of the endoscope 1 by feeding air into the endoscope 1 from the ventilation base 12 in water by operating the air feeding device.

Also, a cap or the like, not shown, for releasing the inside of the endoscope 1 to the atmosphere is detachably provided at the ventilation base 12. The cap or the like is a part of the endoscope 1 used for leaving the endoscope 1 under a negative pressure such as sterilization processing, transport by air or the like. The part as an example releases the inside of the endoscope 1 into the atmosphere so that rubber, not shown, covering the outer periphery of the bending portion 6 does not burst by the negative pressure, for example. Since the ventilation base 12 is provided at a position opposite to a battery 34 housed in a device body 18, which will be described later, with respect to the endoscope main body 1b, the weight balance of the endoscope main body 1b is favorable and the configuration is preferable for improvement of operability.

Figure 6:
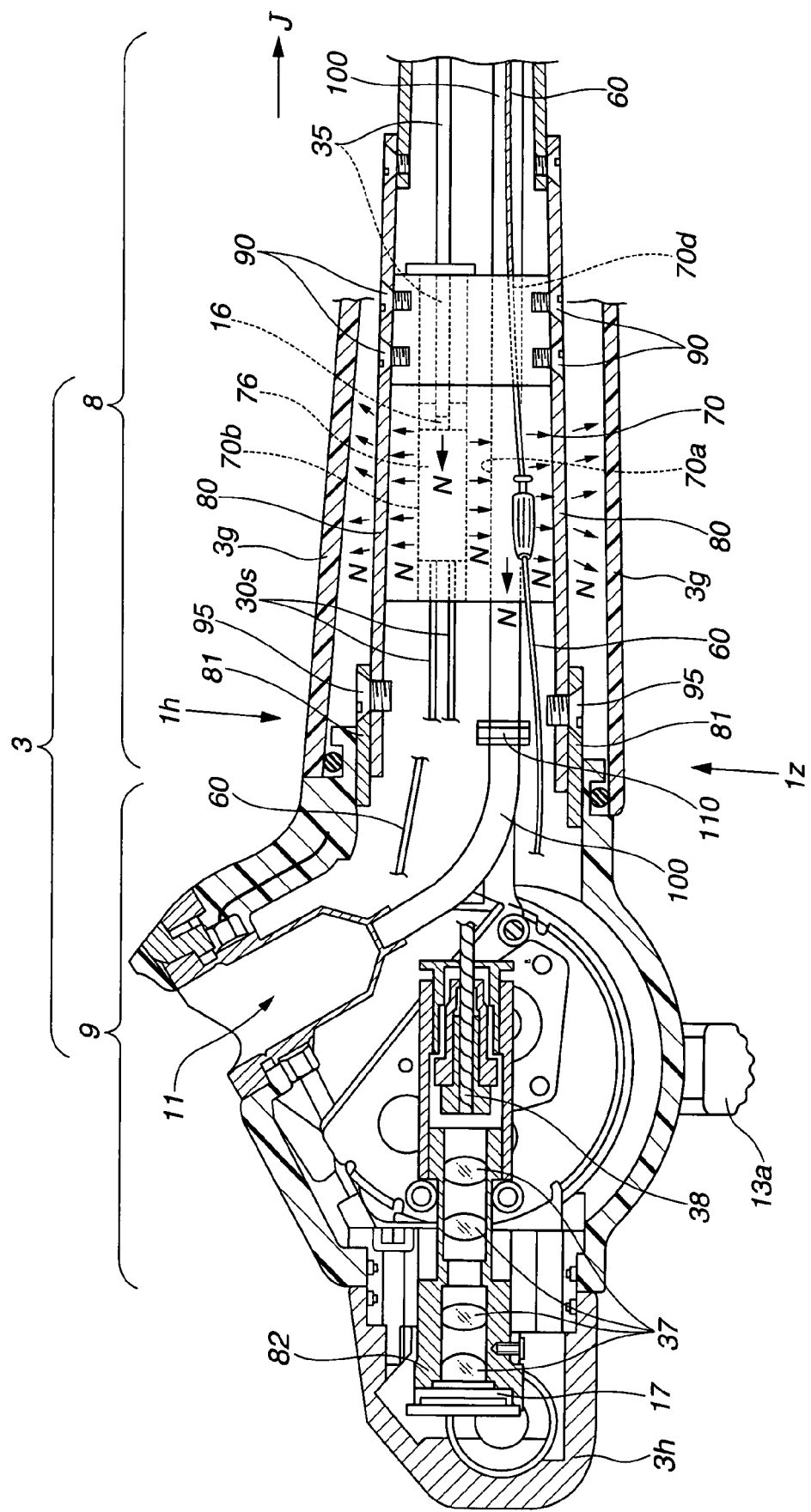
FIG. 6 is a partially enlarged sectional view schematically illustrating an internal configuration of an operation portion of the endoscope in FIG. 1.

Moreover, on a back face 1z side of the endoscope 1 of the operation portion main body 9, a bending operation lever 13 is provided for bending the bending portion 6 in the vertical direction, for example, through a bending operation wire 60 (See FIG. 6).

The bending operation wire 60 has one end fixed to the distal end of a bending piece, not shown, in the bending portion 6 and the other end fixed to a pulley or the like, not shown, disposed in the operation portion 3 and extends through the insertion portion 2 and the operation portion 3.

The bending operation lever 13 is provided at a position proximate to the grasping portion 8 so that it can be operated by the thumb T of the left hand, for example, of the operator grasping the grasping portion 8. Also, the bending operation lever 13 in the L shape comprises a finger hook portion 13a located on the back face 1z side of the endoscope 1 of the operation portion main body 9 and an arm portion 13b continuously provided at the finger hook portion 13a.

In the bending operation lever 13, since the arm portion 13b is rotatably supported pivotally by a rotating shaft 14 penetrating the operation portion main body 9 horizontally in FIG. 1, the finger hook portion 13a is provided at a predetermined position of the operation portion main body 9.

Also, as shown in FIG. 2, on the front 1h side of the endoscope 1 of the operation portion main body 9, an image recording switch 15*a* and an image replay switch 15*b* are provided. The image recording switch 15*a* is turned on when an image displayed on the image display device 4 is to be recorded in a recording medium of a recording control circuit 31 (See FIG. 7), which will be described later. Also, the image replay switch 15*b* is turned on when the recorded image is to be replayed. Also, on the front 1*h* side of the endoscope 1 of the operation portion main body 9 and in the vicinity of an image switch 15, the suction button 11*a* is provided.

Moreover, as shown in FIG. 6, which will be described later, a white light emitting diode 16, for example (hereinafter referred to as LED), which is illuminating means and an illumination portion for supplying illumination light to illuminate the subject, is disposed in the grasping portion 8. Also, in the operation portion main body 9, as shown in FIG. 6, which will be described later, an image pickup device 17 comprised by CCD, CMOS and the like, which is image pickup means and an image pickup device for picking up an image of a portion to be inspected is disposed. The image pickup device 17 constitutes the image pickup device, which is the image pickup means.

The outer shape of the image display device 4 comprises, as shown in FIGS. 1 and 2, the box-type device body 18 substantially in the rectangular solid shape and a tilt lever 19, which is the finger hook portion, extending toward the back face 1*z* side of the endoscope 1 so as to form a plane from the corner portion of one side of the device body 18.

On the upper face of the device body 18 constituting a disposing face 4*h* of an exterior member 4*g*, which will be described later, of the image display device 4 (See FIGS. 8 and 11 for both), as shown in FIG. 5, a monitor portion 21, which is the display portion for displaying an endoscopic image picked up by the image pickup device 17, a POWER indicator lamp 23 lighted when power is on, and a power switch 22 for turning ON/OFF of a power source of the endoscope main body 1*b* are provided.

Also, on the upper face of the tilt lever 19 constituting the disposing face 4*h* of the exterior member 4*g*, which will be described later, of the image display device 4, a still image recording switch 24 which is turned on when an endoscopic image to be recorded is set to a still image and an animated image recording switch 25 which is turned on when an endoscopic image to be recorded is set to an animation are provided.

The still image recording switch 24 and the animated image recording switch 25 may be provided on the upper face of the device body 18 and the power switch 22 may be provided on the upper face of the tilt lever 19. Also, the image recording switch 15*a* and the image replay switch 15*b* may be provided on the upper face of the device body 18 or the upper face of the tilt lever 19.

When the operator erroneously touches the power switch 22 during use of the endoscope 1, the force acting to push in the power switch 22 acts to rotate the image display device 4 around the rotating shaft 55 before the power switch 22 is pressed. In other words, the pressing operation of the power switch 22 is configured to be operated in a state where the operator intentionally holds the device body 18 so that the image display device 4 is not rotated, unexpected touching on the power switch 22 during use of the endoscope 1 and turning it off can be prevented.

Also, as shown in FIG. 1, on one face of the device body 18 on the back face 1*z* side in the endoscope 1, a lid body 26 for storing the battery 34 and a recording medium such as a memory card, not shown, in a storage portion or removing the medium from the storage portion is disposed.

The components disposed in the device body 18 which can be moved by rotation, opening and closing are in the watertight structure. Particularly, the opening/closing lid body 26 is, as shown in FIG. 3, in the structure that water tightness inside the storage portion is surely held by a fixed claw 26*a* provided at a buckle lever 26*b* locked by a side face forming the storage portion of the device body 18.

The image display device 4 is made rotatable with respect to the operation portion main body 9 by the rotating shaft 55, which will be described later, provided penetrating in the right and left direction when seen facing the drawing in FIG. 1 at a connection portion 120 described later (See FIG. 8) between the device body 18 and the operation portion main body 9. In detail, the image display device 4 is, as shown in FIGS. 3 and 4, rotatable around the rotating shaft 55 from a position where the monitor portion 21 is faced up in the direction away from the insertion direction J of the insertion portion 2 to a position where the monitor portion 21 substantially crosses the insertion direction J of the insertion portion 2 (direction along the longitudinal axis of the operation portion 3 on the side of the insertion portion 2) and the monitor portion 21 is faced to the back face 1*z* side in the direction connecting the front face 1*h* and the back face 1*z* substantially perpendicularly (arrow P direction).

Figure 8:
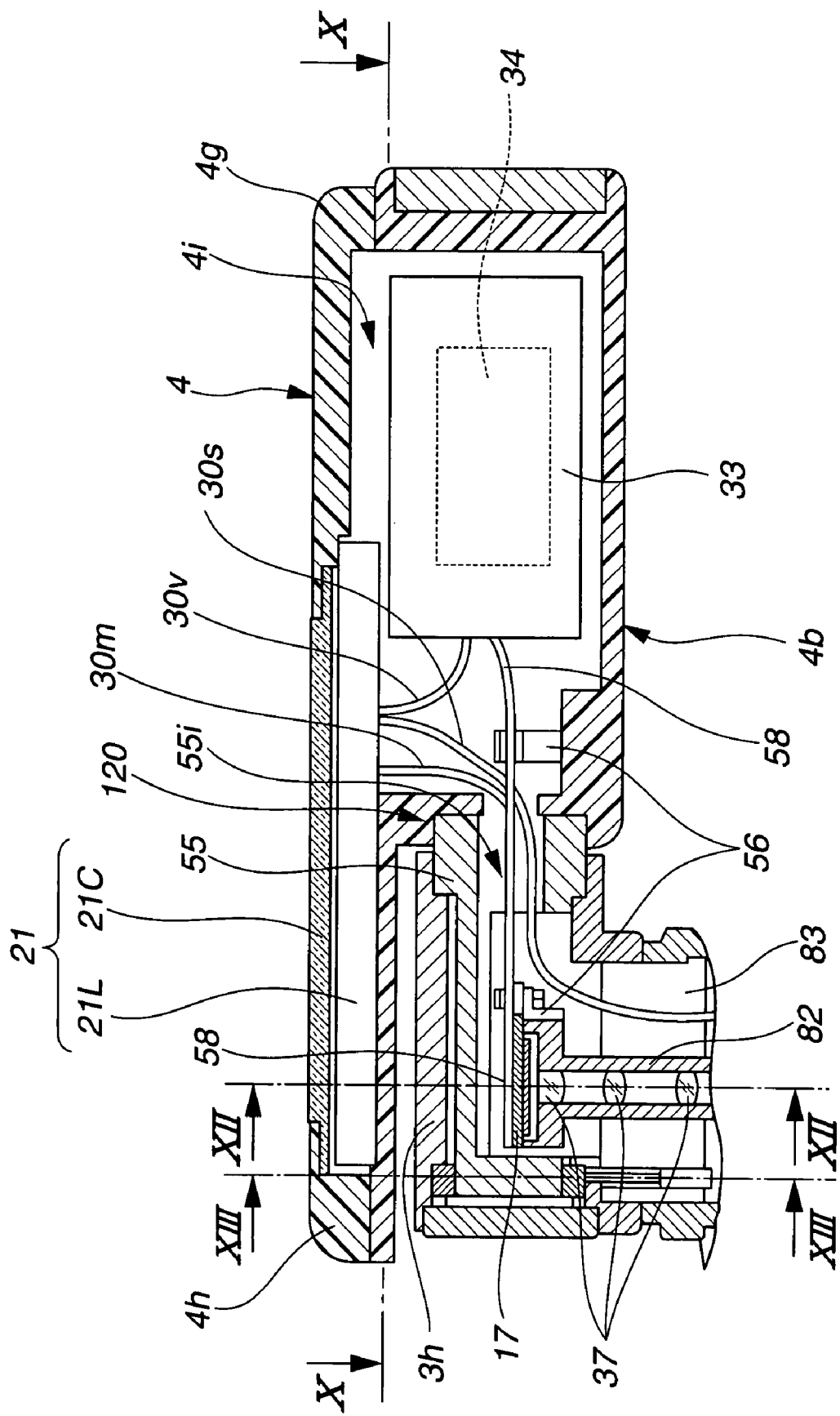
FIG. 8 is a sectional view of a part of the operation portion along VIII-VIII line in FIG. 3 and the image display device.

That is, the image display device 4 is rotatably supported and continuously provided by the rotating shaft 55 disposed in the connection portion 120 at the upper end of the operation portion 3, which is the other end on the side opposite to the one end from which the insertion portion 2 is extended from the operation portion 3 (See FIG. 8). The rotating shaft 55 constitutes the shaft member.

The rotation of the image display device 4 is performed when the tile lever 19 is rotated by the finger cushion of the thumb T of the left hand, for example, of the operator grasping the grasping portion 8. On the upper face of the tilt lever 19, a plurality of projecting portions as slip stoppers 20 (See FIG. 3) are formed. By this, the operator can rotate the tilt lever so as to direct the monitor portion 21 of the image display device 4 in the desired direction without slipping the finger by the slip stopper 20.

In the present embodiment, as shown in FIG. 4, the rotating angle (also referred to as tilt angle) of the monitor portion 21 can be restricted at a predetermined angle without providing a complicated mechanism. Specifically, as shown in FIG. 4, in the device body 18 of the image display device 4, a first abutment portion 18*a* for restricting a rotating position of the device body 18 at a position where the monitor portion 21 is faced upward away from the insertion direction J of the insertion portion 2 and a second abutment portion 18*b* for restricting the rotating position of the device body 18 at a position where the monitor portion 21 is faced toward the back face 1*z* side of the endoscope 1, which is a direction P substantially crossing insertion direction J are provided.

The first and the second abutment portions 18*a*, 18*b* are brought into contact with predetermined positions on the outer surface of the exterior member 3*h* of the operation portion main body 9 constituting the connection portion 120 between the device body 18 and the operation portion main body 9 and restrict rotation of the device body 18 with the monitor portion 21 at an angular position shown by a solid line and a broken line in FIG. 4.

In the present embodiment, the rotation of the device body 18 is restricted so that the monitor portion 21 is faced upward away form the insertion direction J by bringing the first abutment portion 18*a* into contact with the outer surface of the exterior member 3*h* of the operation portion main body 9 (solid line portion in FIG. 4). On the other hand, by bringing the second abutment portion 18b into contact with the outer surface of the exterior member 3h of the operation portion main body 9, the rotation of the device body 18 is restricted so that an angle made by the surface of the monitor portion 21 and the P direction, which is the horizontal direction, becomes 60 degrees (broken line portion in FIG. 4). Needless to say, not limited to the above, the shape or the position of the first, second abutment portions 18a, 18b may be changed in various ways so that the rotating angle of the device body 18 variably changing the facing direction of the monitor portion 21 is restricted at a desired angle.

Next, the configuration to dispose the LED 16 at the operation portion 3 will be described referring to FIG. 6. FIG. 6 is a partially enlarged sectional view schematically illustrating the internal configuration of the operation portion of the endoscope of FIG. 1.

As shown in FIG. 6, inside the grasping portion 8 of the operation portion 3 blocked in a water tight manner by the exterior member 3g, metal frames 80 constituting a plate-state heat transfer frame with the section formed in the semicircular state are extended along the back face 1z side and the front face 1h side of the endoscope 1 of the exterior member 3g so that they are opposed to each other along the longitudinal axis of the grasping portion 8. Each metal frame 80 is fixed to the exterior member 3g and each interposing plate 81 fixed to the inner face of the exterior member 3g with a screw 95.

Also, in a space formed by the two opposing metal frames 80 in the grasping portion 8, the suction pipe line 100, the image guide 38, the bending operation wire 60, and a light guide bundle 35 are extended. In this space, a cable 30s is also extended from a power supply control circuit 30, which will be described later, to the LED 16 for transmitting power supplied by the battery 34 to the LED 16.

Moreover, in the space formed by the two opposing metal frames 80 in the grasping portion 8, a light emitting means fixing member (also referred to as light emitting portion fixing member) 70 is fixed with a screw 90, which is a mounting member.

The light emitting means fixing member 70 is formed by a solid substantially columnar member, for example, and is constituted by a heat transfer member such as aluminum, brass or the like. Also, in the light emitting means fixing member 70, through holes 70a to 70e (only the through hole 70c is not shown) are formed along the longitudinal axis of the grasping portion 8 as shown in FIG. 6. The light emitting means fixing member 70 may have only a portion between the through hole 70a and the through hole 70b constituted by a heat transfer member.

Into the through hole 70a, the middle portion of the suction pipe line 100, which is a fluid pipe line extended through the grasping portion is inserted so that it is brought into close contact with the inner periphery of the through hole 70a. Also, at the through hole 70b, an LED base 76, which will be described later, and the light guide bundle 35 are inserted/disposed.

Also, inside the through hole 70b, the LED base 76 made of a favorable heat transfer material to which the LED 16 is fixed to be abutted against one end face of the light guide bundle 35 is inserted to be installed. To the LED base 76, the cable 30s extended from the power supply control circuit 30 (See FIG. 7), which will be described later, for supplying power to the LED 16 is connected. Also, the LED base 76 is fixed to be brought into close contact with the inner periphery of the through hole 70b.

Into the through hole 70c, the image guide 38 is inserted. On the other hand, to the through holes 70d, 70e, the bending operation wire 60 is inserted.

Also, the proximal end portion of the image guide 38 is fixed to a lens frame 82 for fixing the image pickup device 17 and a light collecting lens 37. A mounting method of the image pickup device 17 to the lens frame 82 will be described later.

Next, the internal configuration of the endoscope 1 centering on the image pickup system and the illumination optical system will be described referring to FIGS. 7 to 13.

Figure 9:
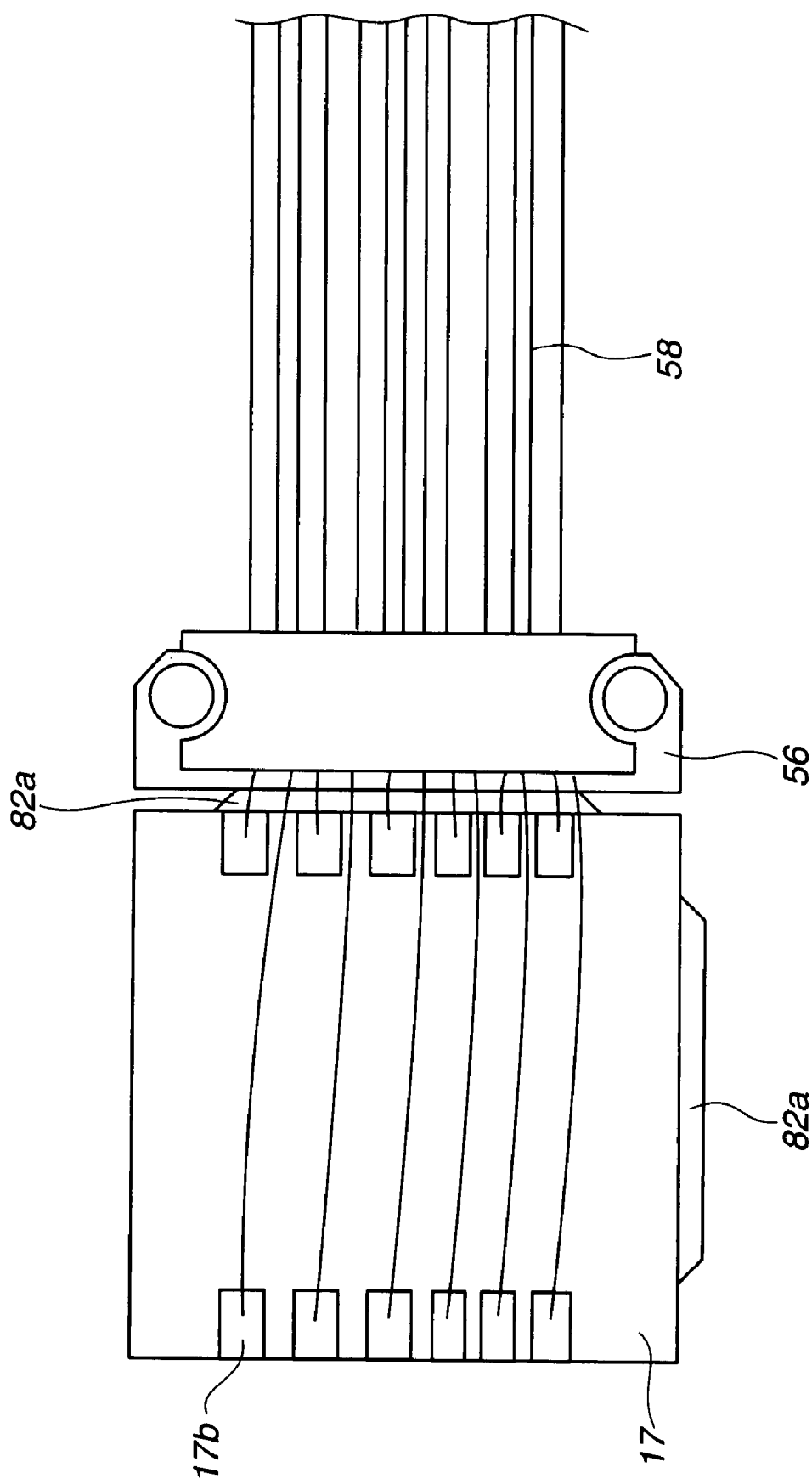
FIG. 9 is a top view of an image pickup device fixed to a lens frame in FIG. 8.
Figure 10:
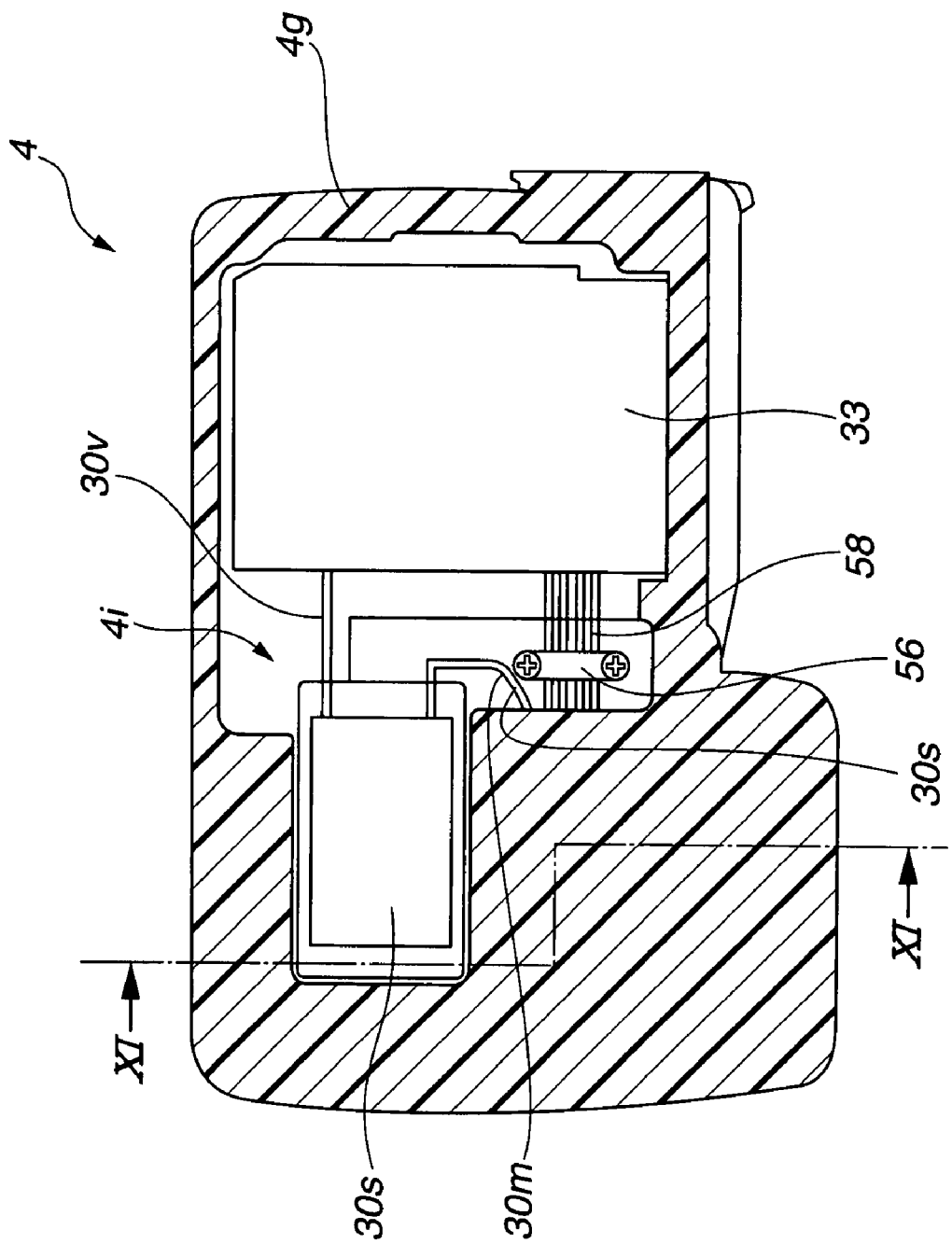
FIG. 10 is a sectional view of the image display device along X-X line in FIG. 8.
Figure 11:
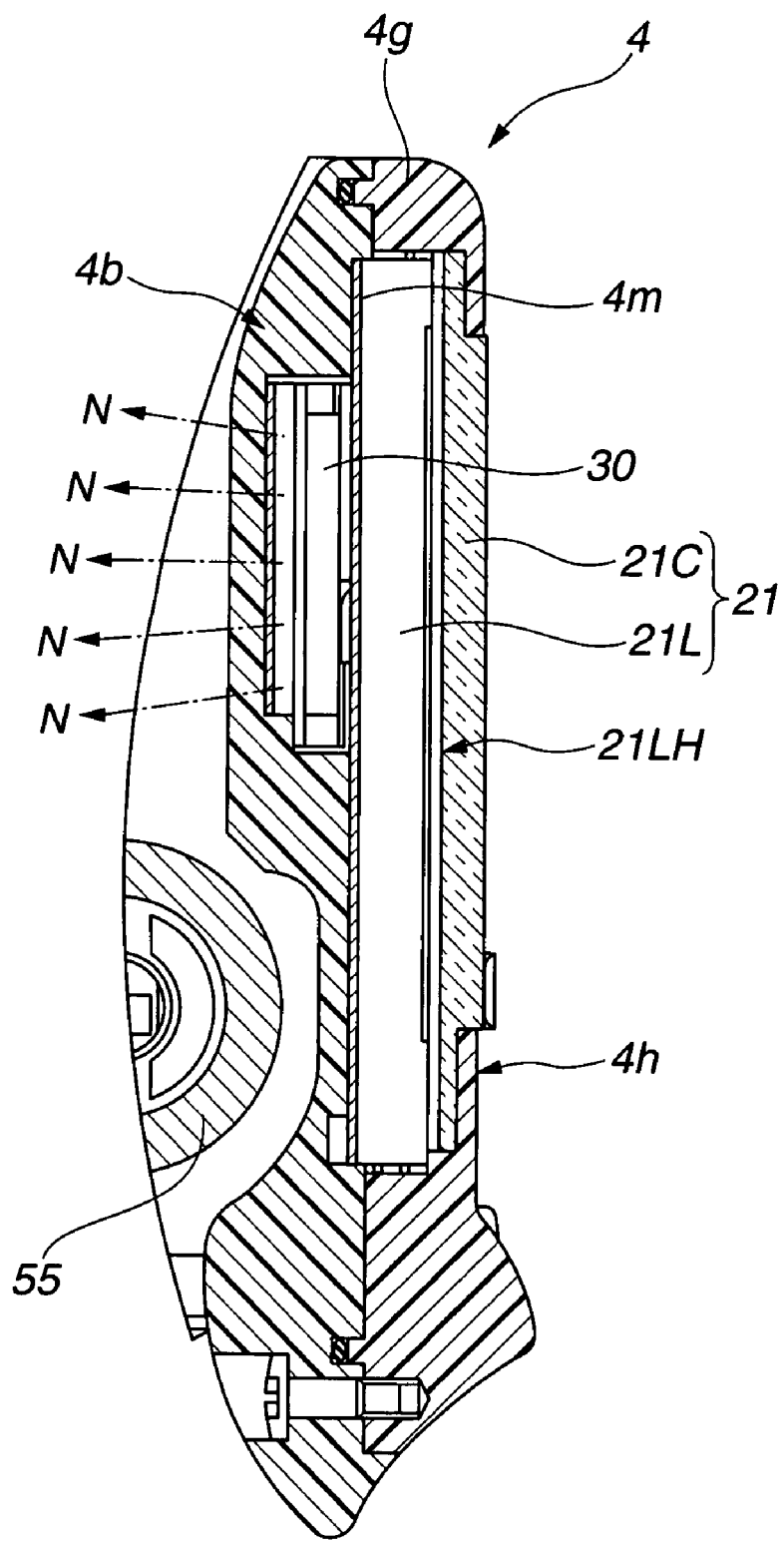
FIG. 11 is a sectional view of the image display device along XI-XI line in FIG. 10.
Figure 12:
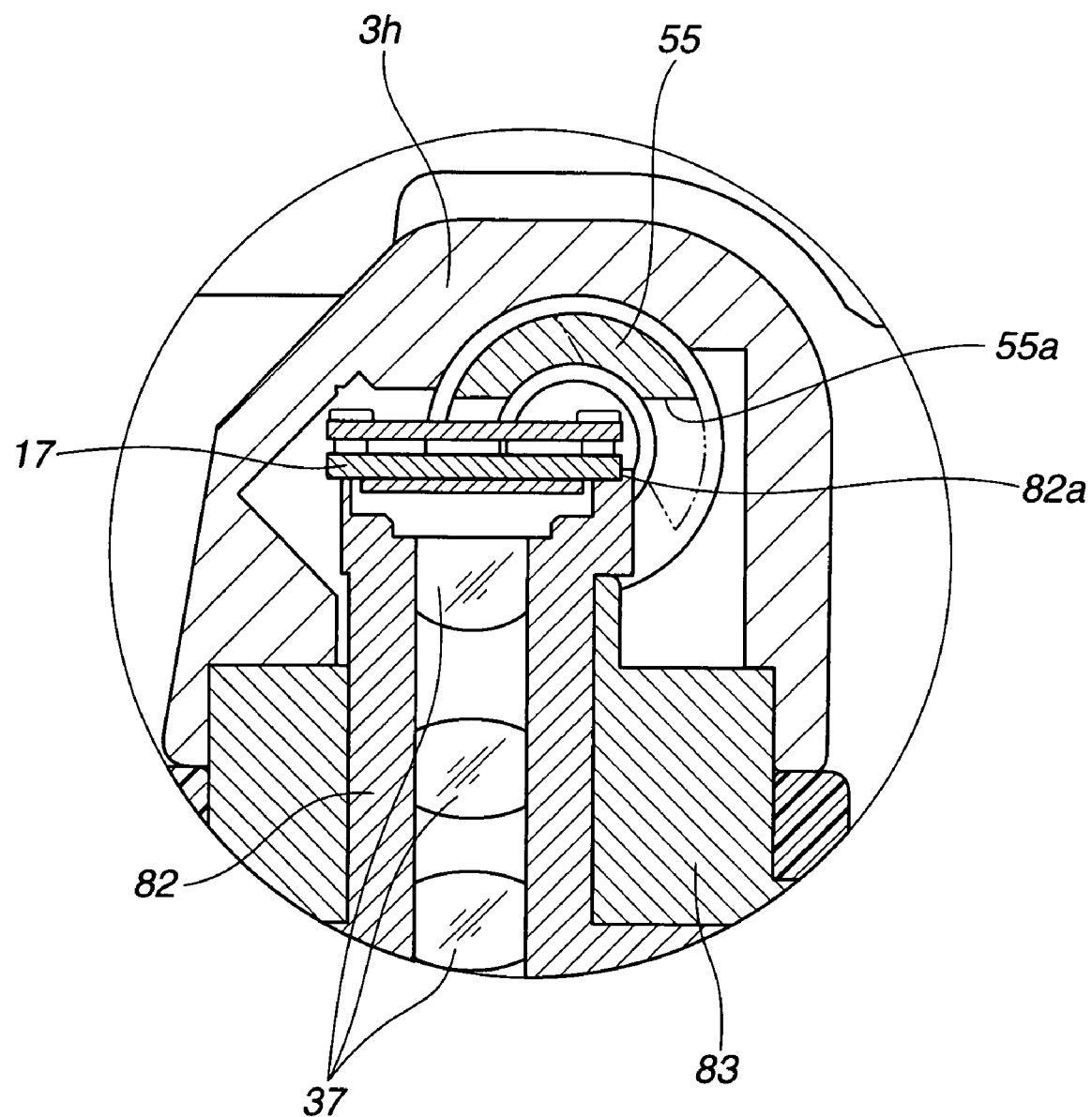
FIG. 12 is a sectional view of a rotating shaft in the operation portion along XII-XII line in FIG. 8 and the vicinity of the lens frame.
Figure 13:
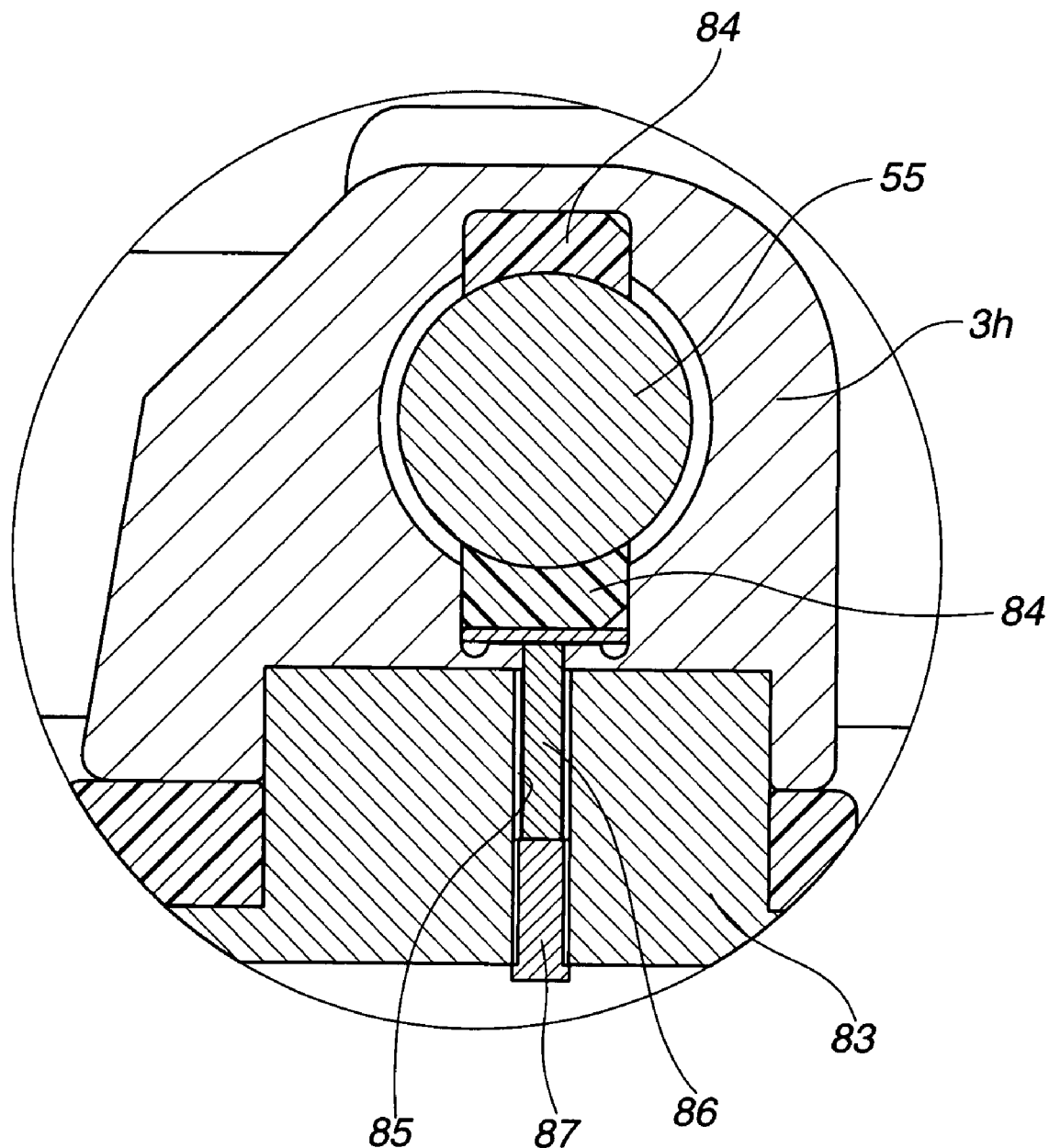
FIG. 13 is a sectional view of the vicinity of the rotating shaft in the operation portion along XIII-XIII line in FIG. 8.

FIG. 7 is a block diagram schematically illustrating the internal configuration of the endoscope in FIG. 1 centering on an image pickup system and an illumination optical system, FIG. 8 is a sectional view of a part of the operation portion along VIII-VIII line in FIG. 3 and the image display device, FIG. 9 is a top view of an image pickup device fixed to a lens frame in FIG. 8, FIG. 10 is a sectional view of the image display device along X-X line in FIG. 8, FIG. 11 is a sectional view of the image display device along XI-XI line in FIG. 10, FIG. 12 is a sectional view of a rotating shaft in the operation portion along XII-XII line in FIG. 8 and the vicinity of the lens frame, and FIG. 13 is a sectional view of the vicinity of the rotating shaft in the operation portion along XIII-XIII line in FIG. 8.

As shown in FIG. 7, in an internal space 4i blocked by the exterior member 4g, which is a frame body of the image display device 4 in the water tight state, in addition to the above-mentioned monitor portion 21 and the battery 34, the power supply control circuit 30, which is a driving circuit, the recording control circuit 31, which is recording means and constitutes a recording portion, a display control circuit 32, and an image pickup device control circuit 33, which is image pickup means, are provided.

On the disposing face 4h of the exterior member 4g of the image display device 4, a recess state groove 4m (See FIG. 11) is provided. This groove 4m is formed so that a planar area becomes substantially equal to the size of the above-mentioned monitor portion 21.

Also, in the groove 4m shown in FIG. 11, a display device such as an LCD, which is a display member (hereinafter referred to as LCD) 21L and a cover member 21C covering a display surface 21LH of the LCD 21L are fitted and disposed. The LCD 21L and the cover member 21C constitute a part of the monitor portion 21. The exterior member 4g of the image display device 4 holds the monitor portion 21.

Also, as shown in FIG. 7, the light guide bundle 35 and the image guide 38 are extended from the insertion portion 2 inside the endoscope 1 to the grasping portion 8 of the operation portion 3. Also, from the distal end portion 5 to the operation portion main body 9, the suction pipe line 100 is extended. Moreover, from the bending portion 6 to the operation portion main body 9, the bending operation wire 60 (not shown in FIG. 7) is extended.

Also, as shown in FIG. 7, the illumination light from the LED 16 provided in the grasping portion 8 is radiated to one end face of the light guide bundle 35 located to be abutted against the LED 16. After that, the illumination light from the LED 16 is transmitted from the one end face of the light guide bundle 35 to the other end face of the light guide bundle 35 located at the distal end portion 5. And the illumination light guided through the light guide bundle 35 is illuminated in a predetermined range toward a portion to be inspected 50 within the body cavity by an illumination lens 36 provided at the distal end side of the other end face of the light guide bundle 35 at the distal end portion 5.

An image by reflective light from the portion to be inspected 50 illuminated by the illumination light enters the other end of the image guide 38 through an image pickup lens 40 provided at the distal end portion 5 and an objective lens 39. After that, the image of the portion to be inspected 50 by the reflective light is transmitted to one end of the image guide 38. Then, the image of the portion to be inspected 50 by the reflective light is formed on the image pickup device 17 from the one end of the image guide 38 through the light collecting lens 37 provided in the operation portion main body 9.

The power supply control circuit 30 is, as shown in FIG. 11, disposed at a position not in contact with the wall surface of a back face 4b side forming the internal space 4i in a planar space on the back face 4b side of the exterior member 4g rather than the monitor portion 21 in the internal space 4i of the image display device 4. That is, the power supply control circuit 30 is disposed at a position in a space different from the LED 16 disposed in the above-mentioned grasping portion 8, that is, in the internal space 4i of the image display device 4 so that the heat by the power supply control circuit 30 does not give an influence to the operator.

The power supply control circuit 30 outputs power supplied from the battery 34 to the LED 16, the image pickup device 17, the monitor portion 21, and recording control circuit 31, the display control circuit 32, and the image pickup device control circuit 33, respectively, as driving power corresponding each of them.

To the image pickup device 17 and the LED 16 disposed in the operation portion 3, the driving power is outputted through the cables 30s, 30m inserted through a space 55i in the rotating shaft 55 in the connection portion 120 between the operation portion 3 and the image display device 4 as shown in FIGS. 8 and 10. Also, to the recording control circuit 31, the display control circuit 32, and the image pickup device control circuit 33, the driving power is outputted through a cable 30v in the internal space 4i of the image display device 4.

Also, the power supply control circuit 30 comprises the power switch 22 and is powered on/off by the power switch 22. The battery 34 comprises a secondary battery which can be used repeatedly by being charged.

An image of the portion to be inspected 50 picked up by the image pickup device 17 is outputted from the image pickup device 17 to the image pickup device control circuit 33 by an image pickup cable 58 having one end connected to the image pickup device 17 and the other end to the image pickup device control circuit 33.

The image pickup cable 58 is also inserted through the space 55i in the rotating shaft 55 constituting the shaft member at the connection portion 120. Also, the image pickup cable 58 has its middle portion held by a pair of clamp members 56 provided oppositely in the vicinity of the rotating shaft 55 in the operation portion main body 9 and the image display device 4 as shown in FIG. 8, for example, so that a connection portion between the image pickup device 17 and the mage pickup cable 58 is not given a load even if it is twisted by rotating action of the image display device 4. Therefore, the image pickup cable 58 between the pair of clamp members 56 is prevented from being twisted at a portion held by both sides of the pair of clamp members 56 even though a part might be twisted by the rotating action of the image display device 4.

Also, as shown in FIG. 8, the image pickup device 17 of the present embodiment is arranged in the exterior member 3h of the operation portion main body 9. On the other hand, the image pickup device control circuit 33, which is the image processing portion, is arranged within the storage portion, not shown, in the device body 18 of the image display device 4 at a separated position via the rotating shaft 55 with respect to the image pickup device 17.

The rotating shaft 55 for rotatably connecting the device body 18 of the image display device 4 and the operation portion main body 9 is provided at the exterior member 4g of the image display device 4 and is a cylindrical body for rotatably supporting the exterior member 3h of the operation portion main body 9. The material of the cylindrical rotating shaft 55 is formed by an electromagnetic wave shielding member such as metal.

The rotating shaft 55 may be further formed by coating the entire inner peripheral surface of the cylindrical body with the electromagnetic wave shielding member such as silver. Also, in order to eliminate influence of a radiation noise to the image pickup device control circuit 33, which is the image processing portion, the entire inner peripheral surface of the exterior member 4g (See FIG. 8) containing the battery 34 may be coated with an electromagnetic wave shielding member such as silver.

By this, the rotating shaft 55 can shield the radiation noise from the image pickup cable 58 inserted therethrough at the connection portion 120. Thus, the endoscope 1 of the present embodiment can prevent leakage of the radiation noise to outside the endoscope, and the influence of the radiation noise to the electronic equipment can be minimized.

The image pickup device 17 is mounted to the lens frame 82 by the following mounting method. When described specifically, in the present embodiment, in order to position the image pickup device 17 to the lens frame 82 (See FIG. 8) in a smaller area and with accuracy, as shown in FIG. 9, abutment portions 82a, 82a are formed at least two sides of the lens frame 82. And in the present embodiment, the image pickup device 17 is positioned to the lens frame 82 so that the side face portions of two crossing sides of the image pickup device 17 to be installed are abutted against the two abutment portions 82a, 82a. The abutment portions 82a, 82a are formed in the stepped shape.

By this, the image pickup device 17 is fixed in the state that it is positioned with accuracy by bringing the two side face portions into contact with the two abutment portions 82a (the other abutment portion 82a is not shown) formed in the stepped shape of the lens frame 82, as shown in FIG. 12, which will be described later. The plurality of abutment portions 82a of the lens frame 82 are provided at least at the two sides of the lens frame 82 in the present embodiment, but it is needless to say that they may be provided at more than two sides such as three sides or four sides.

Also, as shown in FIGS. 8 and 12, the image pickup device 17 is provided inside the rotating shaft 55 so as not to be interlocked with the rotating action of the rotating shaft 55, but in the present embodiment, the rotating shaft 55 incorporating the image pickup device 17 is configured so that the rotating shaft 55 is not expanded outward to enlarge the shape of the operation portion main body 9.

That is, as shown in FIG. 12, at a portion close to the image pickup device 17 of the rotating shaft 55, a notch 55a for avoiding contact with the image pickup device 17 is provided. By this, the rotating shaft 55 is not brought into contact with the image pickup device 17 even if it is rotated with the rotation of the image display device 4 but can contain the image pickup device 17 inside. Thus, the operation portion main body 9 can be formed without enlarging the shape thereof.

Moreover, the endoscope 1 of the present embodiment is configured so that the rotation resistance when the image display device 4 is rotated can be changed. That is, as shown in FIG. 13, a pair of resistance bodies 84 are provided at the exterior member 3h at which the rotating shaft 55 is slidably disposed so that the resistance bodies hold the outer peripheral surface of the rotating shaft 55 from two directions and are brought into contact. One of the resistance bodies 84 is fixed in the exterior member 3h and the other of the resistance bodies 84 is configured so that a contact force (pressing force) to the outer peripheral surface of the rotating shaft 55 is adjustable by a screwing amount of an adjusting pin 87 through a contact portion 86.

The contact portion 86 is inserted through a mounting hole 85 provided at a connecting member 83 and is moved in the direction of the outer peripheral surface of the rotating shaft 55 by screwing the adjusting pin 87 into a thread hole formed at the lower part in the mounting hole 85. The resistance body 84 is formed of a fluororesin or the like.

By this, in the endoscope 1 of the present embodiment, the adjusting pin 87 is adjusted by a predetermined screwing amount in the mounting hole 85 provided at the connecting member 83 in advance during the manufacturing process, and the outer peripheral surface of the rotating shaft 55 is held between the two resistance bodies 84 from the two directions. And in the endoscope 1, through the contact portion 86 of the other resistance body 84, the contact force (pressing force) to the outer peripheral surface of the rotating shaft 55 by the one resistance body 84 is changed and the rotation resistance of the rotating shaft 55, that is, the rotation resistance of the image display device 4 can be adjusted to a desirable state.

The above-mentioned rotation resistance mechanism such as the two resistance bodies 84 is provided on the side opposite to the image pickup device control circuit 33 with respect to the image pickup device 17, that is, on the side face portion of the operation portion main body 9 on the side opposite to the direction of the image display device 4. Thus, the endoscope 1 of the present embodiment is formed with a small lateral width dimension of the operation portion main body 9, and size increase is prevented.

Also, in the endoscope 1 of the present embodiment, the rotating shaft 55, which is a connection portion between the operation portion main body 9 and the device body 18 of the image display device 4, is provided, and as shown in FIG. 8, the side face portion of the operation portion main body 9 on the side opposite to the direction of the image display device 4 is blocked inside the exterior member 3h so that the rotating shaft 55 is kept water tight. By this, the endoscope 1 of the present embodiment is configured so that cleaning efficiency and water tightness are sufficiently ensured.

Returning to FIG. 7 again, the image pickup device control circuit 33 electrically connected by the image pickup cable 58 from the image pickup device 17 makes an image of the portion to be inspected 50 picked up by the image pickup device 17 into a signal and outputs the signal to the recording control circuit 31 and the display control circuit 32. The image pickup device control circuit 33, the display control circuit 32 and the like constitute the image processing portion.

A recording medium such as an XD picture card can be detachably attached to the recording control circuit 31. To the recording control circuit 31, an input signal is supplied from the image switch 15 provided at the operation portion main body 9 (See FIG. 2) and the still image recording switch 24 and the animated image recording switch 25 provided at the image display device 4 (See FIG. 1 for both).

According to the input signal from these switches, the recording control circuit 31 executes control of recording, replay and the like of the signal of an endoscopic image as a still image or an animated image. That is, the recording control circuit 31 stores an image of the portion to be inspected 50 converted into a signal by the image pickup device control circuit 33 in a recording medium and outputs the stored signal to the display control circuit 32 according to input of an instruction signal by the image replay switch 15b for replay, pause or the like.

The display control circuit 32 images the signal from the recording control circuit 31 or the image pickup device control circuit 33 and displays an endoscopic image on the monitor portion 21.

In this case, if the center of the image pickup device 17 is displaced from the center of the image guide 38, a displaced endoscopic image is displayed on the monitor portion 21. Then, in the present embodiment, if the center of the image pickup device 17 is displaced from the center of the image guide 38, correction processing is performed by the display control circuit 32.

Specifically, the display control circuit 32 executes an image centering function for processing to align a position to clip an endoscopic image on the basis of image pickup by the image pickup device 17 with a position of the image guide 38. By this, without providing a mechanical positioning mechanism but by executing the image centering function by the display control circuit 32, even if the center of the image pickup device 17 is displaced from the position of the center of the image guide 38, an endoscopic image with aligned center positions is displayed on the monitor portion 21.

Also, the recording control circuit 31 supplies an instruction signal to the power control circuit 30 for power supply to the LED 16, the image pickup device 17, and the mage pickup device control circuit 33 according to signal input from the switches 15, 24, 25.

The endoscope 1 of the present embodiment configured as above is supplied with power from the power supply control circuit 30 of the image display device 4, when the power switch 22 is turned on, and started in an image display mode and then, an image recorded in the recording control circuit 31 is displayed on the monitor portion 21. In this state, power is not supplied from the power supply control circuit 30 to the LED 16 and the image pickup device 17.

After that, when the still image recording switch 24 is turned on by the operator to change to a still image recording standby state, power is also supplied to the LED 16 and the image pickup device 17 from the power supply control circuit 30, an image pickup signal photoelectrically converted is transmitted from the image pickup device 17 to the image pickup device control circuit 33, the display control circuit 32, and the monitor portion 21 in this order, and an image being observed is displayed on the monitor portion 21 in real time.

If the still image is to be recorded in this state, when the image recording switch 15a is turned on by the operator, an image signal is taken into the recording control circuit 31 from the image pickup device control circuit 33, and the still image is recorded in an internal memory, which is a recording medium of the recording control circuit 31. After the recording, an image being observed is automatically displayed on the monitor portion 21 again.

After that, when the image replay switch 15b is turned on by the operator, an image signal is outputted from the recording control circuit 31 to the display control circuit 32, and the recorded still image is displayed on the monitor portion 21. After that, when the image replay switch 15b is turned off by the operator, an image being observed is displayed on the monitor portion 21 instead of display of the still image.

Also, when the animated image recording switch 25 is turned on by the operator, the state is changed to an animated recording standby state, and in this case, too, a photoelectrically converted image pickup signal is transmitted from the image pickup device 17 to the image pickup device control circuit 33, the display control circuit 32, and the monitor portion 21 in this order, and an image being observed is displayed on the monitor portion 21 in real time.

If an animated image is to be recorded in this state, when the image recording switch 15*a* is turned on by the operator, an animated image is recorded in the internal memory of the recording control circuit 31 similarly to the above.

During recording of the animated image, an image signal is outputted in real time to the display control circuit 32 by either the image pickup device control circuit 33 or the recording control circuit 31, and an observed image is displayed on the monitor portion 21 in real time.

After that, when the image recording switch 15*a* is turned off by the operator, the recording is stopped, and an image being observed is displayed on the monitor portion 21. If an animated image is to be replayed subsequently, when the image replay switch 15*b* is turned on by the operator, the same control as the still image replay is carried out. After the animated image is replayed, the same control as the above-mentioned finishing of the still image replay is executed, and the state is returned to the above state at start.

Next, action of the present embodiment configured as above will be described. The action described below will be on an electromagnetic wave shielding action by the rotating shaft 55 rotatably connecting the device body 18 of the image display device 4 and the operation portion main body 9.

First, when the power switch 22 of the endoscope 1 is turned on, power is supplied from the power supply control circuit 30 of the image display device 4 and the device is started in the image replay mode. After that, when the still image recording switch 24 is turned on by the operator to bring the device into the still image recording standby state, for example, power is also supplied form the power supply control circuit 30 to the LED 16 and the image pickup device 17.

In this state, an image pickup signal is transmitted from the image pickup device 17 to the image pickup device control circuit 33, the display control circuit 32, and the monitor portion 21 in this order and an image being observed is displayed on the monitor portion 21 in real time.

At this time, there is a fear that a radiation noise such as an electromagnetic wave is generated from the image pickup device 17 and the image pickup cable 58. Particularly in a configuration provided with the rotating shaft 55 constituting the connection portion between the image display device 4 and the operation portion main body 9 through which the image pickup cable 58 is inserted, the radiation noise might leak outside the endoscope via the rotating shaft 55.

Then, in the endoscope 1 of the present embodiment, as shown in FIG. 8, the image pickup device 17 is arranged within the exterior member 3*h* of the operation portion main body 9, while the image pickup device control circuit 33, which is the image processing means and constitutes the image processing portion, is arranged within the storage portion, not shown, in the device body 18 of the image display device 4 at the position separated from the image pickup device 17 via the rotating shaft 55.

Moreover, the rotating shaft 55 of the present embodiment for rotatably connecting the device body 18 of the image display device 4 and the operation portion main body 9 is provided at the exterior member 4*g* of the image display device 4 and formed in the cylindrical shape using an electromagnetic wave shielding member such as metal to be slidably engaged with the exterior member 3*h* of the operation portion main body 9. And through the rotating shaft 55, the image pickup cable 58 is inserted.

By this, the radiation noise from the image pickup cable 58 inserted through the rotating shaft 55 is shielded in the rotating shaft 55 forming the connection portion 120.

Also, when the power switch 22 of the endoscope 1 is turned on, a heat N is radiated from the power supply control circuit 30 (See FIG. 11). At this time, the power supply control circuit 30 is provided so as to be located on the back face side of the monitor portion 21 observed by the operator in the internal space 4*i* blocked by the exterior member 4*g* of the image display device 4, more specifically, on the back face 4*b* side of the exterior member 4*g*. By this, the heat N is discharged from the back face 4*b* constituting a heat radiation portion separated from the operator as shown in FIG. 11 in the direction separated from the operator.

The configuration for discharging the heat N may be located in the direction facing the upper face where the monitor portion 21 is separated away from the insertion direction J of the insertion portion 2 or in the direction facing the back face 1*z* side of the endoscope 1, which is the direction P substantially crossing the insertion direction J (longitudinal axis of the operation portion 3).

As described above, according to the endoscope 1 of the present embodiment, since the rotating shaft 55 is formed in the cylindrical shape using an electromagnetic wave shielding member such as metal, which is an electromagnetic wave shielding member, and moreover, the image pickup cable 58 is inserted through the rotating shaft 55, the radiation noise from the image pickup cable 58 inserted through the rotating shaft 55 can be surely shielded in the rotating shaft 55 forming the connection portion 120. Thus, since the leakage of the radiation noise to outside of the endoscope 1 can be prevented, influence of the radiation noise on the electronic equipment can be minimized.

Also, in the endoscope 1 of the present embodiment, when the power supply control circuit 30 is to be disposed in the internal space 4*i* covered by the exterior member 4*g* of the image display device 4, it is disposed on the back face 4*b* side of the exterior member 4*g* rather than the monitor portion 21 in the internal space 4*i*. By this, if heat is generated with driving of the power supply control circuit 30, the generated heat N is radiated toward the front face 1*h* side of the endoscope 1 from the back face 4*b* of the exterior member 4*g* of the image display device 4, which is the back face side of the monitor portion 21. Thus, the endoscope 1 of the present embodiment can surely discharge the heat N of the power supply control circuit 30 in the direction surely avoiding the operator observing the monitor portion 21 located on the back face 1*z* side of the endoscope 1.

Moreover, in the endoscope 1 of the present embodiment, the LED 16 is provided in the operation portion 3 and the power supply control circuit 30 in the image display device 4. Therefore, in the endoscope 1 of the present embodiment, since the LED 16 and the power supply control circuit 30 are provided at locations separated from each other, generation of a locally heated spot by heat radiation from the LED 16 and the power supply control circuit 30 can be prevented. That is, the endoscope 1 of the present invention does not give a sense of discomfort to the operator by local heat radiation since distribution efficiency of heat generated from the LED 16 and the power supply control circuit 30 is improved.

In the present embodiment, a medical endoscope is exemplified as the endoscope 1, but the same effect as that of the present embodiment can be obtained when the endoscope is applied to an industrial endoscope.

From the above, according to the endoscope of the present invention, since leakage of the radiation noise to outside of the endoscope can be prevented by inserting the image pickup cable through the cylindrical electromagnetic wave shielding member constituting the connection portion between the operation portion and the display device so as to shield the radiation noise from the image pickup cable, the influence of the radiation noise on the electronic equipment can be advantageously minimized.

That is, according to the present invention, by inserting the image pickup cable through the cylindrical electromagnetic wave shielding member constituting the connection portion between the operation portion and the display device so as to shield the radiation noise from the image pickup cable, an endoscope which can surely prevent leakage of the radiation noise to outside of the endoscope can be realized.

Also, the invention described in the above embodiment is not limited to the description of the embodiment but various deformations are possible at a practical stage within a range not departing from its gist. Moreover, the above-mentioned embodiment includes inventions at various stages, and various inventions are extracted from appropriate combination of a plurality of disclosed constituent features.

For example, even if some constituent features are deleted from all the constituent features shown in the above-mentioned embodiment, the configuration after the deletion of the constituent features can be extracted as the invention, provided that the effects described in the effect of the invention can be obtained.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope with an electromagnetic wave shield, comprising:
    an insertion portion to be inserted into a subject;
    an operation portion continuously provided on the proximal end side of the insertion portion;
    an image pickup device provided in the operation portion for picking up an image of a portion to be inspected of the subject;
    a display device provided at the operation portion to be rotatable with respect to the operation portion and provided with a display portion displaying a picked up image of the portion to be inspected picked up by the image pickup device;
    an image processing portion provided at the display device and processing an image pickup signal of the portion to be inspected picked up by the image pickup device;
    an image pickup cable electrically connecting the image processing portion and the image pickup device to each other; and
    an electromagnetic wave shielding member provided at a connection portion between the operation portion and the display device, through which the image pickup cable is inserted and arranged, and provided with a notch for avoiding contact with the image pickup device when the display device is rotated.

2. The endoscope with an electromagnetic wave shield according to claim 1, wherein the electromagnetic wave shielding member is a cylindrical body in which the image pickup device is provided.

3. The endoscope with an electromagnetic wave shield according to claim 2, wherein an entire inner peripheral surface of the cylindrical body is coated with an electromagnetic wave shielding material.

4. The endoscope with an electromagnetic wave shield according to claim 2, wherein the electromagnetic wave shielding material is silver.

5. The endoscope with an electromagnetic wave shield according to claim 2, wherein the cylindrical body is a shaft member rotatably connecting the operation portion and the display device to each other around an axis substantially perpendicular to an insertion axis direction of the insertion portion such that a direction of the display portion of the display device is variable between a position where the display portion is faced to be substantially parallel with the insertion axis direction of the insertion portion and a position where the display portion is faced to be substantially perpendicular to the insertion axis direction of the insertion portion.

6. The endoscope with an electromagnetic wave shield according to claim 5, wherein the shaft member is formed by metal.

* * * * *